United States Patent

Kuronuma et al.

[11] Patent Number: 5,326,693
[45] Date of Patent: * Jul. 5, 1994

[54] METHOD FOR CONCURRENT FERMENTATION OF BASIC AMINO ACID AND ACIDIC AMINO ACID

[75] Inventors: Hideo Kuronuma; Harufumi Miwa; Shigeru Nakamori, all of Kawasaki; Toshimasa Ishii, Yokkaichi; Yasuhiko Yoshihara, Saga, all of Japan

[73] Assignee: Ajinomoto Co., Inc., Tokyo, Japan

[*] Notice: The portion of the term of this patent subsequent to Mar. 23, 2010 has been disclaimed.

[21] Appl. No.: 986,749

[22] Filed: Dec. 8, 1992

Related U.S. Application Data

[62] Division of Ser. No. 655,993, Feb. 15, 1991, Pat. No. 5,196,326.

[30] Foreign Application Priority Data

Feb. 15, 1990 [JP] Japan .................................... 2-34066
Feb. 4, 1991 [JP] Japan .................................... 3-100574

[51] Int. Cl.$^5$ ........................ C12P 13/04; C12P 39/00
[52] U.S. Cl. .................................... 435/42; 435/106; 435/109; 435/110; 435/111; 435/112; 435/113; 435/114; 435/115; 435/840; 435/843
[58] Field of Search .............. 435/42, 106, 109, 110, 435/111, 112, 113, 114, 115, 840, 843

[56] References Cited

U.S. PATENT DOCUMENTS

| | | | |
|---|---|---|---|
| 3,399,114 | 8/1968 | Ohsawa et al. ..................... | 435/112 |
| 3,511,752 | 5/1970 | Tanaka et al. ...................... | 435/112 |
| 3,907,641 | 9/1975 | Nakayama et al. ................. | 435/109 |
| 3,943,038 | 3/1976 | Morinaga et al. .................. | 435/106 |
| 3,971,701 | 7/1970 | Takinami et al. ................... | 435/111 |
| 4,334,020 | 6/1982 | Nakazawa et al. ................. | 435/111 |
| 4,411,991 | 10/1983 | Hirakawa et al. .................. | 435/42 |
| 5,100,782 | 3/1992 | Klages et al. ...................... | 435/42 |
| 5,196,326 | 3/1993 | Kuronuma et al. ................. | 435/106 |

FOREIGN PATENT DOCUMENTS

| | | | |
|---|---|---|---|
| 0113569 | 7/1984 | European Pat. Off. ........... | 435/111 |
| 0136359 | 4/1985 | European Pat. Off. . | |
| 0048091 | 3/1954 | Japan ................................. | 435/106 |
| 0032193 | 3/1978 | Japan ................................. | 435/111 |
| 912353 | 12/1962 | United Kingdom .............. | 435/111 |
| 924035 | 4/1963 | United Kingdom .............. | 435/111 |
| 9012105 | 10/1990 | World Int. Prop. O. . | |

OTHER PUBLICATIONS

Chemical Abstracts, 87:66606e.
Patent Abstracts of Japan, vol. 9, No. 1, (C-259)(1724), (1985).

Primary Examiner—Herbert J. Lilling
Attorney, Agent, or Firm—Oblon, Spivak, McClelland, Maier & Neustadt

[57] ABSTRACT

A basic L-amino acid and an acidic L-amino acid may be concurrently produced by either culturing a basic L-amino acid-producing bacteria under conditions for producing an acidic L-amino acid or mix-culturing a basic L-amino acid-producing bacteria and an acidic L-amino acid-producing bacteria.

10 Claims, No Drawings

METHOD FOR CONCURRENT FERMENTATION OF BASIC AMINO ACID AND ACIDIC AMINO ACID

This is a division of application Ser. No. 07/655,993, filed on Feb. 15, 1991 now U.S. Pat. No. 5,196,326.

BACKGROUND OF THE INVENTION

1. Field of the Invention

The present invention relates to a method for concurrent fermentation of a basic amino acid and an acidic amino acid, which comprises culturing a basic L-amino acid-producing bacteria under conditions for producing an acidic L-amino acid or mix-culturing a basic L-amino acid-producing bacteria and acidic L-amino acid-producing bacteria.

2. Discussion of the Background

Simultaneous production of a basic L-amino acid and an acidic L-amino acid by fermentation is unknown heretofore. It has only been known to accumulate any one of a basic L-amino acid and an acidic L-amino acid in a medium. In this case, when two or more amino acids were recognized in a medium, amino acids other than the desired one were present in such a trace amount (several tens of mg/dl) as by-products.

In other words, a method for simultaneously producing a basic L-amino acid and an acidic L-amino acid in a commercially acceptable accumulation amount by fermentation is as yet unknown, though such a method is expected to be advantageous.

Advantages achieved by concurrent production of a basic L-amino acid and an acidic L-amino acid by fermentation involve possible reduction of the amounts of ionic components in a medium, which results in the prevention of an increase of osmosis during incubation thereby improving fermentation productivity (improve the rate of forming amino acids), reduction and saving of medium components, simplified treatment of fermentation broth (operation for isolating amino acids), reduction in the amount of waste liquid after isolating and obtaining amino acids from the fermentation broth, etc. In particular, reduction in the amount of waste liquid is an advantage which cannot be overlooked at this point of time when keen attention is being currently paid to environmental preservation.

SUMMARY OF THE INVENTION

Accordingly, it is one object of the present invention to provide a method for concurrent production of a basic amino acid and an acidic amino acid by fermentation in a commercially acceptable accumulation amount.

It is another object to provide a method for producing a L-amino acid by fermentation which requires a reduced amount of ionic components.

It is another object to provide a method for producing a L-amino acid by fermentation which produces a reduced amount of waste.

These and other objects, which will become apparent during the course of the following detailed description have been achieved by a method for concurrent fermentation of a basic amino acid and an acidic amino acid which comprises culturing basic L-amino acid-producing bacteria under conditions for producing an acidic L-amino acid or mix-culturing basic L-amino acid-producing bacteria and acidic L-amino acid-producing bacteria.

DETAILED DESCRIPTION OF THE PREFERRED EMBODIMENTS

The basic L-amino acid referred to in the present invention includes L-lysine (Lys), L-arginine (Arg), L-histidine (His) and L-ornithine (Orn) and the acidic L-amino acid includes L-glutamic acid (Glu) and L-aspartic acid (Asp).

A first aspect of the present invention which comprises using basic L-amino acid-producing bacteria and culturing the bacteria under a condition for producing an acidic L-amino acid to simultaneously produce the basic L-amino acid and the acidic L-amino acid by fermentation is described below.

As fermentation medium, nutrient medium or synthetic medium containing carbon sources, nitrogen sources, inorganic salts, growth factors, etc. are used. As the carbon sources, there may be used carbohydrates such as glucose, fructose, sucrose, molasses, starch, starch hydrolysate, fruit juice, etc.; alcohols such as ethanol, methanol propanol, etc.; organic acids such as acetic acid, etc. As the nitrogen sources, there may be used ammonium sulfate, ammonium nitrate, ammonium chloride, ammonium phosphate, ammonium acetate, ammonia, amines, peptone, meat extract, yeast extract, corn steep liquor, casein hydrolysate, various fermentation cells and their digestion products. Where mutants showing auxotrophy are used, substances required are supplemented as authentic materials or natural materials containing the same.

Fermentation is carried out generally under aerobic conditions such as aerial agitation, shake culture, etc. A suitable time for incubation is 2 to 7 days, and a suitable temperature is from 24° to 40° C., preferably 25° to 38° C. A pH value of the culture broth is maintained in a range of 5 to 9. For adjusting the pH, urea, calcium carbonate, ammonia gas, ammonia water, etc. are used.

These fermentation media and conditions for fermentation have been adopted in conventionally known amino acid fermentation. In the process of the present invention, conditions for concurrently producing basic L-amino acids and acidic L-amino acids by fermentation should also be adopted additionally.

These conditions are described below in detail.

Basic L-amino acid-producing bacteria which are conventionally known are generally obtained by subjecting Coryne type bacteria such as bacteria belonging to the genus Brevibacterium, bacteria belonging to the genus Corynebacterium, etc. to a variety of mutation treatments. For example *Brevibacterium lactofermentum* ATCC 13869 is subjected to a mutation treatment using nitrosoguanidine as a mutating agent to produce lysine-producing *Breyibacterium lactofermentum* ATCC 21798, having a resistance to AEC (S-2-aminoethyl-L-cystein).

On the other hand, with acidic L-amino acid-producing bacteria which fall under the Coryne type bacteria, only the cells are proliferated in a medium in which a sufficient amount (10 μg/l or more) of biotin is present and the acidic L-amino acid is hardly accumulated, although these bacteria are generally biotin-auxotrophic. In order to accumulate the acidic L-amino acid, it is necessary to inhibit proliferation of the cells and for this purpose, it is necessary either to use a biotin-poor medium, or, in the case of using a medium where a sufficient amount of biotin is present, to supplement a surfactant such as polyoxyethylene sorbitan monopalmitate (PESP), etc. or a lactam antibiotic such as penicillin, etc., at the initial stage of or during incubation. Basic L-amino acid-producing bacteria induced from the acidic L-amino acid-producing bacteria belonging to such Coryne type bacteria by mutation are still biotin-auxotrophic, but in the case of producing basic L-amino acid by fermentation by the incubation of such bacteria, a sufficient amount of biotin may be present in the medium, unlike the case of producing the acidic L-amino acid by fermentation by incubation of the original acidic L-amino acid-producing bacteria, and it is unnecessary to limit biotin to a low concentration.

Thus, the present inventors cultured the aforesaid basic L-amino acid-producing bacteria using the original acidic L-amino acid-producing bacteria under such a condition that the acidic L-amino acid can be produced by fermentation and have found very unexpectedly that not only the basic L-amino acid but also the acidic L-amino acid could be accumulated concurrently. As a matter of course, the yield of the basic L-amino acid based on the carbon sources decreases and the acidic L-amino acid is accumulated in such an amount that compensates for the decreased yield, in this case.

Therefore, where the basic L-amino acid-producing bacteria are biotin-auxotrophic bacteria as described above, the condition for producing the acidic L-amino acid is either: (1) a medium with a low concentration of biotin; or (2) a medium in which a surfactant, such as polyoxyethylene sorbitan monopalmitate (PESP), polyoxyethylene sorbitan monostearate (PESS), polyoxyethylene sorbitan monolaurate (PESL),etc. or a lactam antibiotic such as penicillin, cephaloridine, or the like is supplemented at the initial stage of or during incubation.

The low biotin concentration refers to a biotin concentration of 0.5 to 10 $\mu g/l$, preferably 1 to 5 $\mu g/l$. By adjusting the amount of biotin to such a concentration, for example, Lys and Glu can be produced. A suitable amount of a surfactant such as polyoxyethylene sorbitan monopalmitate (PESP), etc. or a lactam antibiotic such as penicillin, etc. which are supplemented in the medium at the initial stage or during incubation is approximately 0.01 to 0.5 g/dl, preferably 0.05 to 0.1 g/dl, in the case of the surfactant and approximately 0.1 to 10 U/ml, preferably 1 to 5 U/ml, in the case of a lactam antibiotic. In this way, for example, Lys and Glu can be produced.

Next, the second aspect of the present invention, namely, the method for concurrent fermentation of the basic L-amino acid and the acidic L-amino acid which comprises using the basic L-amino acid-producing bacteria and the acidic L-amino acid-producing bacteria in combination and mix-culturing these bacteria is described below.

It is well known that the basic L-amino acid-producing bacteria and the acidic L-amino acid-producing bacteria are those belonging to Coryne type bacteria such as the genus Brevibacterium the genus Corynebacterium, etc., bacteria belonging to the genus Bacillus such as *Bacillus subtilas*, etc., bacteria belonging to the genus Escherichia such as *Escherichia coli*, etc. These amino acid-producing bacteria may be widely used. The medium used and conditions for fermentation may be those adopted in conventionally known amino acid fermentation described with respect to the first aspect of the present invention.

The conditions for concurrent fermentative production of the basic L-amino acid and the acidic L-amino acid in the second aspect of the invention may be a mere combination of the conditions for accumulating the basic L-amino acid by fermentation using the basic L-amino acid-producing bacteria and the conditions for accumulating the acidic L-amino acid by fermentation using the acidic L-amino acid-producing bacteria. In this case, these two conditions for fermentation may be those described above as the conditions for producing known amino acids, but there is no substantial difference between the former and the latter. The only difference is that either the basic L-amino acid or the acidic L-amino acid-producing bacteria to be mix-cultured is auxotrophic and another is non-auxotrophic. In this case, it is necessary for the auxotrophic bacteria that the required nutrient be supplemented in the medium, but it is unnecessary for the non-auxotrophic bacteria to particularly supplement the nutrient required. Where the auxotrophic bacteria and the non-auxotrophic bacteria are mixed and cultured, the combination of the conditions for culturing both bacteria means that the required nutrient is supplemented to the medium. Where the non-auxotrophic bacteria and the auxotrophic bacteria are mix-cultured to produce the basic L-amino acid with one bacteria and to produce the acidic L-amino acid with another bacteria, amino acid production of the non-auxotrophic bacteria is not adversely affected at all even though the required nutrient is supplemented to the medium.

According to the method (first and second aspects) of the present invention, the basic L-amino acid and the acidic L-amino acid can be concurrently accumulated in a medium in commercially accumulated amounts, namely, in amounts of about 500 mg/dl or more, at the same time, by adopting the conditions for simultaneous fermentation as described above.

In order to isolate and harvest the amino acids produced and accumulated from the fermentation broth, conventional techniques may be used, for example, by means of ion exchange resin technique (for example, firstly adsorbing and isolating the basic amino acid from the fermentation broth with a cation exchange resin and then adsorbing and isolating the acidic amino acid with an anionic exchange resin). For the purpose of using the basic L-amino acid and the acidic L-amino acid as a mixture, it is unnecessary to isolate the amino acids from each other.

Suitable basic L-amino acid-producing bacteria and acidic L-amino acid-producing bacteria for use in the present methods are given in Table I.

| | Suitable Microorganisms | | | | |
|---|---|---|---|---|---|
| | L-amino acid produced[1,4] | | | | |
| Bacteria | Glu | Lys | Arg | His | Asp |
| *Brev. lactofermentum*[2] | 13869 | 21798 | | | |
| | 13655 | 21799 | | | |
| | | 21800 | | | |
| | | 21801 | | | |
| | | 21086 | | | |

-continued

| Bacteria | Suitable Microorganisms L-amino acid produced[1,4] | | | | |
|---|---|---|---|---|---|
| | Glu | Lys | Arg | His | Asp |
| *Brev. flavum* | 14067 | 21475 | 21493 | 21406 | |
| | | 21127 | | 21605 | |
| | | 21128 | | | |
| | | 21129 | | | |
| | | 21474 | | | |
| *Brev. ammoniagenes* | 13745 | 19355 | | | |
| *Brev. roseum* | 13825 | | | | |
| *Brev. saccharolyticum* | 14066 | | | | |
| *Coryne. acetoacidophilum*[3] | 13870 | 21476 | | 21407 | |
| *Coryne. glutamicum* | 21492 | 13286 | 21659 | 21339 | FERM BP-2178 |
| | 39135 | | | | |
| | 39136 | | | | |
| | 39137 | | | | |
| | 39138 | | | | |
| | NRRL B-12138 | | | | |
| *Coryne. acetoglutamicum* | | 21491 | | | |
| *Coryne. lilium* | 15990 | | | | |

[1]All numbers other than those indicated as NRRL and FERM deposit numbers are ATCC deposit numbers.
[2]*Brev.*: *Brevibacterium*.
[3]*Coryne.*: *Corynebacterium*.
[4]number indicated by underline: strain utilized in an Example of the present invention.

As described above, the method for concurrent fermentation of the basic L-amino acid and the acidic L-amino acid is advantageous in various points, which are explained below.

Turning to the reduction of the amount of ionic components in the medium, in the case of the production of Lys, 0.2 to 0.4 M of acidic ions were required to neutralize Lys formed in the single fermentation of Lys according to the prior art. According to the method for concurrent production of Lys and Gly of the present invention, the amount required can be reduced to 0.1 to 0.2 M.

Turning next to the improved fermentation productivity (improved rate of forming the amino acids), for example, in the case of the single production of Lys according to the prior art, the rate of forming Lys per cell and per time was 0.03 to 0.04 hr$^{-1}$. According to the method of concurrent production of Lys and Glu of the present invention, however, the rate of forming Lys and Glu is improved approximately two-fold to 0.06 to 0.08 hr$^{-1}$ in total.

Turning to saving and omission of the medium components, for example, in the case of the production of Lys according to the prior art, 2 to 6 g/dl of ammonium sulfate and ammonia were required as medium components, whereas in the method of the present invention for concurrent production of Lys and Glu, no ammonium sulfate is required and the ammonia required may be 1 g/dl or less.

Turning to the simplified treatment of the fermentation broth (operation for isolation of the amino acids), for example, in the case of the production of Lys according to the prior art, a desalting step was required, but in the method of the present invention for concurrent production of Lys and Glu, the desalting step is unnecessary.

Turning to the reduced load of waste liquid, for example, in the case of the production of Lys according to the prior art, the waste liquid exhausted from its production steps contains nitrogen compounds which should be removed by a treatment with activated sludge or a denitrification treatment subsequent thereto, but in the method of the present invention for concurrent production of Lys and Glu, the nitrogen compounds in the waste liquid can be reduced to almost zero.

Other features of the invention will become apparent in the course of the following descriptions of exemplary embodiments which are given for illustration of the invention and are not intended to be limiting thereof.

EXAMPLES

Example 1 (Concurrent Production of Lys and Glu by Incubation of Lys-producing Bacteria)

An aqueous solution medium containing 140 mg/ml of crude sugar when calculated as sugar, 1 mg/ml of $KH_2PO_4$, 0.4 mg/ml of $MgSO_4.7H_2O$, 10 mg/ml of $FeSO_4.7H_2O$, 20 μg/ml of $MnSO_4.4H_2O$, 5 mg/ml of urea, 5 μl/ml of soybean protein acid hydrolysate "AJI-EKI" (registered trademark), 50 μg/l of biotin and 60 μg/l of thiamine was prepared and 20 ml of the medium was charged into a shake flask of 500 ml volume followed by sterilization for 10 minutes by heating at 115° C.

Lys-producing *Brevibacterium lactofermentum* (ATCC 21798) was inoculated on the medium and cultured at 31.5° C. on a reciprocal shaker. During the incubation, aqueous urea solution having a concentration of 400 mg/ml was supplemented by small portions so as to keep the pH at 6.5 to 8.0.

When the absorbance of a 26-fold dilution of the fermentation broth at 562 μm reached 0.30, 4 mg/ml of PESP (polyoxyethylene sorbitan monopalmitate) was added to terminate the fermentation. The L-lysine and L-glutamic acid accumulated in the fermentation broth was quantitatively determined by liquid chromatography, whereby 30 mg/ml of L-lysine and 22 mg/ml of L-glutamic acid were accumulated.

Using the same medium but supplemented with 25 mg/ml of ammonium sulfate and the same bacteria, fermentation of lysine alone was performed in a similar manner except for adding no PESP during the incubation. The fermentation was completed in 55 hours and 53 mg/ml of L-lysine was accumulated in the fermentation broth.

In the case of the concurrent fermentation of L-lysine and L-glutamic acid, the ion concentration was 0.13 M which was one-half of the 0.28 M in the latter case where L-lysine alone was fermented.

The rate of forming the amino acid was 0.066 hr$^{-1}$ as the total rate of forming L-lysine and L-glutamic acid per cells and per hour, whereas in the fermentation of L-lysine alone, the rate of forming L-lysine was 0.035 hr$^{-1}$.

Comparing the medium components, ammonium sulfate in the initial medium and urea-derived ammonia at the initial stage and for supplementation required 35 mg/ml in total in the case of the latter production of L-lysine alone. In the case of the concurrent production of L-lysine and L-glutamic acid, however, no ammonium sulfate was required and urea-derived ammonia was merely 6 mg/ml in total for the initial addition and supplementation.

The resulting fermentation broth was further treated in a conventional manner using ion exchange resins. A salt concentration in the effluent through the resins which remained after adsorption of L-lysine and/or L-glutamic acid onto the ion exchange resins was as high as 5% in the case of production of L-lysine alone so that desalting was necessary for effectively utilizing the effluent. On the other hand, in the case of concurrent production of L-lysine and L-glutamic acid, the salt concentration was as low as below 2% so that desalting was unnecessary.

The waste liquid, such as the resin washing liquid, etc. was treated by the activated sludge process. In the waste liquid from the production of L-lysine alone, the contained BOD (biochemical oxygen demand) could be removed, but large quantities of nitrogen compounds remained so that it was necessary to perform a denitrification treatment separately. In the waste liquid from the concurrent production of L-lysine and L-glutamic acid, however, particularly large quantities of nitrogen compounds were not noted in the liquid obtained after removing BOD by the activated sludge process.

Example 2 (Concurrent Production of Lys and Glu by Incubation of Lys-Producing Bacteria)

An aqueous solution medium containing 15% of glucose, 0.1% of potassium primary phosphate ($KH_2PO_4$), 0.04% of magnesium sulfate heptahydrate, 2% of ammonium sulfate, 100 µg/l of biotin, 200 µg/l of vitamin $B_1$ hydrochloride, 2 ppm each of iron ions and manganese ions and 1% of "AJI-EKI" pH 7.0, was separately charged in a small glass jar fermenters in an amount of 300 ml each. After sterilization, Lys-producing Brevibacterium flavum (ATCC 21127), which had been previously grown in a bouillon slant at 30° C. for 24 hours, was inoculated on the medium. Then incubation was initiated at 31° C. About 10 hours after, penicillin was supplemented in a concentration of 6 U/ml and the incubation was continued for 18 hours. At the end of the fermentation, 3.75 g/dl of L-Lysine and 2.05 g/dl of L-glutamic acid were produced and accumulated in the medium.

The cells were removed from 1 liter of the fermentation broth by centrifugation and L-Lysine and L-glutamic acid were isolated and purified from the supernatant in a conventional manner using an ion exchange resin to give 28.1 g of L-Lysine-HCl crystals and 18.5 g of Monosodium Glutamate crystals.

Example 3 (Concurrent Production of His and Glu by Incubation of His-Producing Bacteria)

His-producing bacteria, Brevibacterium flavum (ATCC 21406) was inoculated on the following seed culture medium followed by aerial spinner culture at 31° C. for 20 hours.

Seed culture medium:

Aqueous solution medium containing 3 g/dl of glucose, 0.3 g/dl of urea, 50.1 g/dl of $KH_2PO_4$, 0.04 g/dl of $MgSO_4.7H_2O$, 2 ppm each of Fe and Mn ions, 200 µg/l of biotin, 300 µg/l of thiamine hydrochloride, 1 ml/dl of soybean protein hydrochloric acid hydrolysate (total nitrogen of 7%), 0.5 g/dl of yeast extract and 0.5 g/dl of meat extract, pH 7.2.

On the other hand, 300 ml of the main fermentation medium having the following composition was separately charged into a small glass jar fermenter of 1 liter volume followed by sterilization. On the medium was inoculated 15 ml of the seed culture medium described above. Spinner culture was initiated at 31° C. by passing 1/1 volume per minute of air.

Main fermentation medium;

Aqueous solution medium containing 10 g/dl of glucose, 0.5 g/dl of ammonium sulfate, 0.1 g/dl of $KH_2PO_4$, 0.04 g/dl of $MgSO_4.7H_2O$, 2 ppm each of Fe and Mn ions, 100 µg/l of biotin, 200 µg/l of thiamine hydrochloride and 2 ml/dl of soybean protein hydrochloric acid hydrolysate (total nitrogen of 7%), pH 7.2.

When the pH decreased during the incubation at 31° C., ammonia gas was supplemented to keep the pH at 7.0 to 7.5. After 10 hours passed after the initiation of incubation, polyoxyethylene sorbitan monopalmitate was added in a concentration of 0.4 g/dl and incubation was continued.

Eighteen hours later, 0.8 g/dl of L-histidine and 1.2 g/dl of L-glutamic acid were accumulated in the fermentation broth. The cells were removed from the fermentation broth by centrifugation and 1.9 g of L-histidine crystals and 2.8 g of L-glutamic acid crystals were obtained in a conventional manner.

Example 4 (Concurrent Production of Glu and Lys by Mix-Culturing Glu-Producing Bacteria and Lys-Producing Bacteria)

Glu-producing bacteria, Corynebacterium glutamicum (NRRL B-12138) and Lys-producing bacteria, Brevibacterium lactofermentum (ATCC 21799) were scraped by one platinum loop each from each slant and each was inoculated on 50 ml of seed culture aqueous solution medium having the following composition followed by aerial spinner culture at 31° C. for 18 hours to prepare each seed culture solution.

| Composition of seed culture medium: | |
| --- | --- |
| Glucose | 1.5% |
| Ammonium acetate | 0.3% |
| Urea | 0.1% |
| $KH_2PO_4$ | 0.1% |
| $MgSO_4.7H_2O$ | 0.04% |
| $Fe^{++}$ | 2 ppm |
| $Mn^{++}$ | 2 ppm |
| Biotin | 50 µg/l |
| Thiamine hydrochloride | 200 µg/l |
| Soybean protein hydrochloric acid hydrolysate concentrate (total nitrogen of 7%) | 3% |
| pH 7.5 | |

On the other hand, 300 ml of the main fermentation medium having the following composition was separately charged in a small glass jar fermenter of 1 liter volume followed by sterilization in a conventional manner. On the medium was simultaneously inoculated 15 ml each of the seed culture medium described above. Spinner culture was initiated at 31° C. by passing 1/1 volume per minute of air.

| Main fermentation medium: | |
| --- | --- |
| Glucose | 2% |
| Ammonium acetate | 0.5% |
| Urea | 0.2% |
| KHPO$_4$ | 0.1% |
| MgSO$_4$.7H$_2$O | 0.04% |
| Fe$^{++}$ | 2 ppm |
| Mn$^{++}$ | 2 ppm |
| Biotin | 50 µg/l |
| Thiamine hydrochloride | 60 µg/l |
| Soybean protein hydrochloric acid hydrolysate concentrate (total nitrogen of 7%) | 3% |
| pH 7.5 | |

A mixture of acetic acid and ammonium acetate (mixing ratio of acetic acid:ammonium acetate = 1:0.25 in molar ratio; concentration of acetic acid in the mixture was 60%) was continuously or intermittently added to the medium so as to keep the pH of the medium between 7.2 and 8.0. Inoculation was carried out at 30° C. for 72 hours.

The results indicate that 37 g/l of L-glutamic acid and 54 g/l of L-lysine were accumulated.

Example 5 (Concurrent Production of Asp and Arg by Mix-Culturing Asp-Producing Bacteria and Arg-Producing Bacteria)

Asp-producing bacteria, *Corynebacterium glutamicum* (FERM BP-2178) and Arg-producing bacteria, *Brevibacterium flavum* (ATCC 21493) were independently inoculated on a seed culture aqueous solution medium having the following composition followed by aerial spinner culture at 30° C. for 18 hours.

Composition of seed culture medium:
3% of glucose, 0.1% of KH$_2$PO$_4$, 0.04% of MgSO$_4$.7H$_2$O, 2 ppm of Fe$^{++}$, 2 ppm of Mn$^{++}$, 3 ml/dl of AJI-EKI, 5 µg/l of biotin, 300 µg/l of vitamin B$_1$ hydrochloride and 0.3% of urea, pH 7.2.

On the other hand, 300 ml of the main fermentation medium having the following composition was separately charged in a small glass jar fermenter of 1 liter volume followed by sterilization. Each of the above seed culture media was simultaneously inoculated by 15 v/v %. Aerial spinner culture was initiated at 31° C. at 1500 r.p.m. by passing 1/1 volume per minute of air.

Composition of main fermentation medium:
1.5% of ethyl alcohol, 0.5% of ammonium sulfate, 0.1% of KH$_2$PO$_4$, 0.04% of MgSO$_4$ 7H$_2$O, 2 ppm of Fe$^{++}$, 2 ml/dl of AJI-EKI (registered trademark), 5 µg/l of biotin, and 300 µg/l of vitamin B$_1$ hydrochloride, pH 7.2.

When the pH decreased during the incubation, ammonia gas was supplemented to keep the pH between 7.0 to 7.5. Ethyl alcohol was supplemented when its concentration was reduced to about 0.1%, while monitoring its consumption by gas chromatography.

Forty-eight hours after the incubation, 1.30 g/dl of L-aspartic acid and 1.05 g/dl of L-arginine were produced in the fermentation broth. In a conventional manner using an ion exchange resin, 2.18 g of L-aspartic acid crystals and 2.18 g of L-arginine crystals were obtained from the fermentation broth.

Example 6 (Concurrent Production of Asp and His by Mix-Culturing Asp-Producing Bacteria and His-Producing Bacteria)

An aqueous solution medium containing 13 g/dl of sucrose, 0.5 g/dl of urea, 0.1 g/dl of KH$_2$PO$_4$, 0.04 g/dl of MgSO$_4$.7H$_2$O, 2 ppm each of Fe and Mn ions, 5 µg/l of biotin, 200 µg/l of thiamine hydrochloride and 0.3 ml/dl of soybean protein hydrochloric acid hydrolysate "AJI-EKI" (total nitrogen of 7%), adjusted to pH 7.2 was prepared and 20 ml of the medium was separately charged into a shake flask of 500 ml volume. After sterilization, Asp-producing bacteria, *Brevibacterium flavum* (FERM BP-2178) and His-producing bacteria, *Brevibacterium flavum* (ATCC 21406), which had been previously grown on bouillon slants, were inoculated in the same flask followed by spinner culture at 31° C. for 72 hours. During the incubation, an aqueous urea solution having a concentration of 40 g/dl was supplemented by small portions to keep the pH between 6.5 to 8.0. In the fermentation broth, 0.95 g/dl of L-aspartic acid and 0.85 g/dl of L-histidine were accumulated.

The cells were removed from the fermentation broth in a conventional manner, and the resulting supernatant was purified in a conventional manner using an ion exchange resin to give 1.75 g of L-aspartic acid crystals and 1.6 g of L-histidine crystals.

Example 7 (Concurrent Production of Glu and Lys by Mix-Culturing Glu-Producing Bacteria and Lys-Producing Bacteria)

An aqueous solution medium containing 50 mg/ml of glucose, 2 mg/ml of urea, 1 mg/ml of KH$_2$PO$_4$, 0.4 mg/ml of MgSO$_4$.7H$_2$O, 10 µg/ml of FeSO$_4$.7H$_2$O, 8 µg/ml of MnSO$_4$.4H$_2$O, 5 µl/ml of soybean protein acid hydrolysate "AJI-EKI" 10.0 µg/dl of thiamine hydrochloride and 0.25 µg/dl of biotin was prepared and 20 ml of the medium was separately charged into a shake flask of 500 ml volume followed by sterilization with heating at 115° C. for 10 minutes. Glu-producing bacteria, *Brevibacterium lactofermentum* (ATCC 13869) and Lys-producing bacteria, *Brevibacterium lactofermentum* (ATCC 21800) were inoculated on the medium. While shaking, incubation was performed at 31.5° C. During the incubation, an aqueous urea solution having a concentration of 450 mg/ml was supplemented in small portions to keep the pH between 6.5 to 8.0. The incubation was completed in 30 hours.

L-glutamic acid and L-lysine accumulated in the fermentation broth were quantitatively determined. As the result, 10.5 mg/ml of L-glutamic acid and 15.3 mg/ml of L-lysine were accumulated.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for concurrent fermentative production of a basic L-amino acid and an acidic L-amino acid, which comprises (a) culturing a basic L-amino acid-producing bacteria belonging to the genus Brevibacterium or the genus Corynebacterium under a condition for producing an acidic L-amino acid, wherein said basic L-amino acid-producing bacteria is biotin-auxotropic and said condition for producing an acidic L-amino acid is (i) a biotin-poor medium, containing 0.5 to 10 μg/l of biotin, or (ii) a medium containing a sufficient amount of biotin and either a surfactant or a lactam type antibiotic, incorporated into said medium at the initial stage or during the incubation, wherein said basic L-amino acid-producing bacteria is selected from the group consisting of *Brevibacterium lactofermentum, Brevibacterium flavum, Brevibacterium ammoniagenes, Corynebacterium acetoacidophilum, Corynebacterium glutamicum* and *Corynebacterium acetoglutamicum*; and (b) recovering said basic L-amino acid and said acidic L-amino acid.

2. A method for concurrent fermentative production of a basic L-amino acid and an acidic L-amino acid, which comprises (a) culturing a basic L-amino acid-producing bacteria belonging to the genus Brevibacterium or the genus Corynebacterium under a condition for producing an acidic L-amino acid, wherein said basic L-amino acid-producing bacteria is biotin-auxotropic and said condition for producing an acidic L-amino acid is (i) a biotin-poor medium, containing 0.5 to 10 μg/l of biotin, or (ii) a medium containing a sufficient amount of biotin and either a surfactant or a lactam type antibiotic, incorporated into said medium at the initial stage or during the incubation, wherein said basic L-amino acid-producing bacteria is selected from the group consisting of *Brevibacterium lactofermentum* ATCC 21798, *Brevibacterium lactofermentum* ATCC 21799, *Brevibacterium lactofermentum* ATCC 21086, *Brevibacterium flavum* ATCC 21128, *Brevibacterium flavum* ATCC 21129, *Brevibacterium flavum* ATCC 21406, *Brevibacterium flavum* ATCC 21605, *Brevibacterium ammoniagenes* ATCC 19355, *Corynebacterium acetoacidophilum* ATCC 21476, *Corynebacterium acetoacidophilum* ATCC 21407, *Corynebacterium glutamicum* ATCC 13286, *Corynebacterium glutamicum* ATCC 21659, *Corynebacterium glutamicum* ATCC 21339, and *Corynebacterium acetoglutamicum* ATCC 21491; and (b) recovering said basic L-amino acid and said acidic L-amino acid.

3. The method of claim 1, wherein said condition for producing an acidic L-amino acid is (i) a biotin-poor medium, containing 0.5 to 10 μg/l of biotin.

4. The method of claim 1, wherein said condition for producing an acidic L-amino acid is (ii) a medium containing a sufficient amount of biotin and either a surfactant or a lactam antibiotic; wherein said surfactant is selected from the group consisting of polyoxyethylene sorbitan monopalmitate, polyoxyethylene sorbitan monostearate, and polyoxyethylene sorbitan monolaurate; and wherein said lactam antibiotic is selected from the group consisting of penicillin and cephaloridine.

5. The method of claim 1, wherein said basic L-amino acid-producing bacteria is *Brevibacterium lactofermentum*.

6. The method of claim 1, wherein said basic L-amino acid-producing bacteria is *Brevibacterium flavum*.

7. The method of claim 1, wherein said basic L-amino acid-producing bacteria is *Brevibacterium ammoniagenes*.

8. The method of claim 1, wherein said basic L-amino acid-producing bacteria is *Corynebacterium acetoacidophilum*.

9. The method of claim 1, wherein said basic L-amino acid-producing bacteria is *Corynebacterium glutamicum*.

10. The method of claim 1, wherein said basic L-amino acid-producing bacteria is *Corynebacterium acetoglutamicum*.

* * * * *

UNITED STATES PATENT AND TRADEMARK OFFICE
CERTIFICATE OF CORRECTION

PATENT NO. : 5,326,693
DATED : Jul. 5, 1994
INVENTOR(S) : Hideo Kuronuma et al

It is certified that error appears in the above-indentified patent and that said Letters Patent is hereby corrected as shown below:

Column 5, Table 1, column entitled "Asp", "FERM BP-2178" should move down one line.

Column 9, line 56, "MgSO$_4$ 7H$_2$O," should read --MgSO$_4$.7H$_2$O,--.

Column 11, Claim 2, line 30, after "ATCC 21799", insert

--*Brevibacterium lactofermentum* ATTC 21800, *Brevibacterium lactofermentum* ATCC 21801,--;

line 31, after "ATCC 21086, insert --*Brevibacterium flavum* ATCC 21475, *Brevibacterium flavum* ATCC 21127,--;

line 32, after "ATCC 21129, insert --*Brevibacterium flavum* ATCC 21474, *Brevibacterium flavum* ATCC 21493--.

Signed and Sealed this

Twenty-third Day of January, 1996

Attest:

BRUCE LEHMAN

*Attesting Officer*     *Commissioner of Patents and Trademarks*